US012186517B2

(12) United States Patent
Modlish et al.

(10) Patent No.: US 12,186,517 B2
(45) Date of Patent: Jan. 7, 2025

(54) HEMOSTASIS VALVE FOR SHEATH ASSEMBLY

(71) Applicant: ABIOMED, INC., Danvers, MA (US)

(72) Inventors: John Matthew Modlish, Danvers, MA (US); Glen R. Fantuzzi, Danvers, MA (US); Christopher Nason Korkuch, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 481 days.

(21) Appl. No.: 17/097,582

(22) Filed: Nov. 13, 2020

(65) Prior Publication Data
US 2021/0146111 A1      May 20, 2021

Related U.S. Application Data

(60) Provisional application No. 62/935,300, filed on Nov. 14, 2019.

(51) Int. Cl.
*A61M 39/06*      (2006.01)
*A61M 25/09*     (2006.01)
(Continued)

(52) U.S. Cl.
CPC ......... *A61M 39/0606* (2013.01); *A61M 25/09* (2013.01); *A61M 29/00* (2013.01);
(Continued)

(58) Field of Classification Search
CPC .. A61M 39/0606; A61M 39/06; A61M 39/20; A61M 25/0097; A61M 39/22;
(Continued)

(56) References Cited

U.S. PATENT DOCUMENTS 4,895,565 A * 1/1990 Hillstead ........... A61M 39/0606
5,409,463 A 4/1995 Thomas et al.
(Continued)

FOREIGN PATENT DOCUMENTS

CN     201469870 U   5/2010
CN     202876024 U   4/2013
(Continued)

OTHER PUBLICATIONS

Eccles, Peter J. An Introduction to Mathematical Reasoning: numbers, sets and functions. Cambridge University Press, 2010.
(Continued)

*Primary Examiner* — Lauren P Farrar
*Assistant Examiner* — Kathleen Paige Farrell
(74) *Attorney, Agent, or Firm* — Botos Churchill IP Law LLP

(57) ABSTRACT

An introducer sheath assembly for percutaneously delivering a medical device that maintains hemostasis in a patient. The assembly has a hub, a hub cap and a hemostasis valve. The introducer sheath assembly has a longitudinal axis and a lumen formed therein. The hemostasis valve has a frame portion and a valve portion, the valve portion having a plurality of slits that are offset through the thickness of the valve portion therein and an extension of the frame portion formed from an incompressible material. The extension of the frame portion is received by a valve seat feature in the hub, when the valve is received by the hub. The valve seat feature also receives a seating portion of the hub cap as the hub and hub cap are advanced into engagement, the seating portion of the hub cap advanced into the valve seat feature subjecting the incompressible extension of the frame portion to a compressive force.

18 Claims, 17 Drawing Sheets

(51) Int. Cl.
*A61M 29/00* (2006.01)
*A61M 60/135* (2021.01)

(52) U.S. Cl.
CPC ..... *A61M 2039/062* (2013.01); *A61M 60/135* (2021.01); *A61M 2205/0216* (2013.01); *A61M 2207/00* (2013.01)

(58) Field of Classification Search
CPC .. A61M 39/00; A61M 39/24; A61M 39/0613; A61M 2039/0633; A61M 2039/064; A61M 2039/0653; A61M 2039/2426; A61M 39/045; A61M 2039/062; A61M 2039/0626; A61M 25/0662; A61M 2039/0235; A61M 2039/068; A61M 2039/0072; A61M 2039/246; A61M 2039/0273; A61M 25/01; A61B 17/3462; A61B 17/3498; A61B 2017/00592; A61B 2017/00862; A61B 2017/3464; Y10T 137/7885; Y10T 137/7879; F16K 15/144
See application file for complete search history.

(56) References Cited

U.S. PATENT DOCUMENTS

| | | | |
|---|---|---|---|
| 5,520,655 A | | 5/1996 | Davila et al. |
| 7,736,296 B2 | | 6/2010 | Siess et al. |
| 11,524,152 B1* | | 12/2022 | Leeflang et al. .. A61M 39/0606 |
| 2001/0041872 A1* | | 11/2001 | Paul, Jr. ............ A61M 39/0606 |
| 2004/0127855 A1 | | 7/2004 | Core |
| 2016/0157873 A1* | | 6/2016 | Griffin et al. ..... A61M 39/0613 |
| 2017/0080200 A1* | | 3/2017 | Bickhart et al. .. A61M 39/0606 |
| 2017/0312491 A1 | | 11/2017 | Ryan et al. |
| 2017/0361083 A1 | | 12/2017 | Sutton |
| 2018/0015277 A1* | | 1/2018 | Stephens et al. ..... A61M 39/22 |
| 2018/0318571 A1* | | 11/2018 | Rieckmann et al. ........................ A61M 39/0693 |

FOREIGN PATENT DOCUMENTS

| | | |
|---|---|---|
| CN | 203169824 U | 9/2013 |
| CN | 103623500 A | 3/2014 |
| CN | 103957978 A | 7/2014 |
| CN | 203763666 U | 8/2014 |
| CN | 104174107 A | 12/2014 |
| CN | 102811760 B | 7/2015 |
| CN | 109952125 A | 6/2019 |
| CN | 110167626 A | 8/2019 |
| EP | 0411605 A1 | 2/1991 |
| JP | H01139077 A | 5/1989 |
| WO | 2012021406 A2 | 2/2012 |
| WO | 2013096694 A1 | 6/2013 |
| WO | 2019090351 A2 | 5/2019 |

OTHER PUBLICATIONS

International Search Report and Written Opinion for Application No. PCT/US20/60501 dated Feb. 24, 2021.

First Office Action issued in Chinese Patent Application No. 2020800794673 on Dec. 25, 2023 (21 pp.).

Office Action for Corresponding Japanese Application No. 2022-527940 dated Oct. 1, 2024, 11 pgs.

* cited by examiner

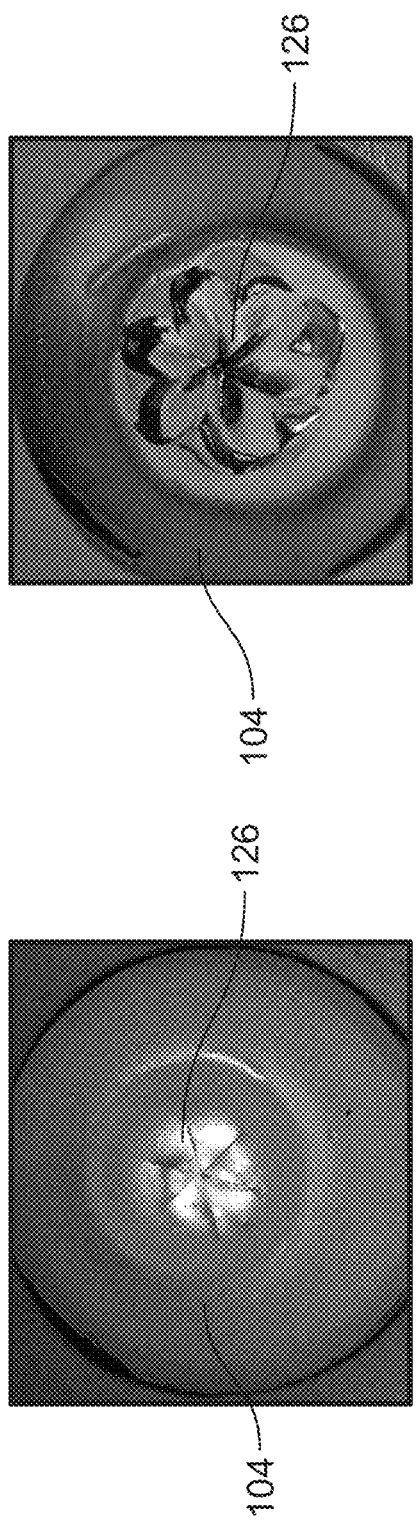
FIG. 8A
FIG. 8B
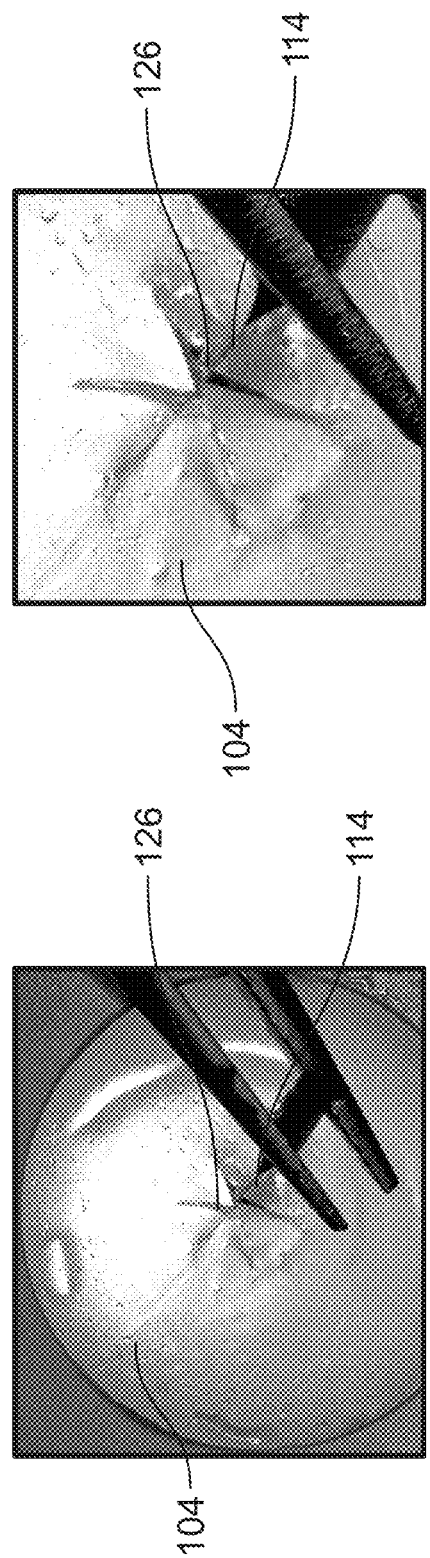
FIG. 8C
FIG. 8D

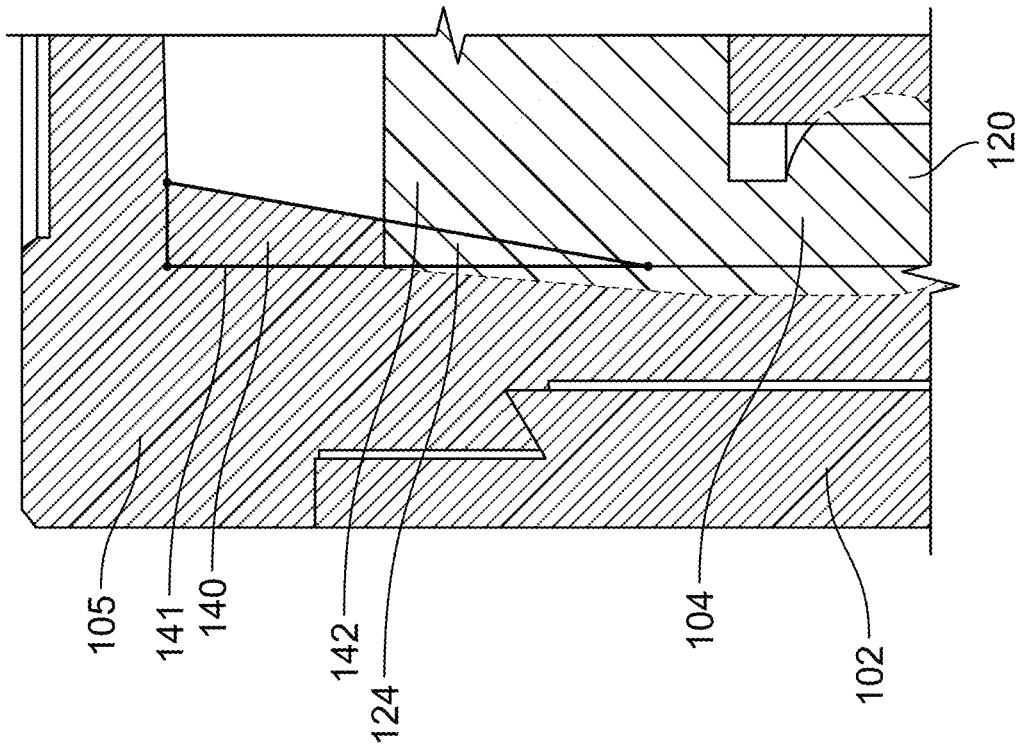
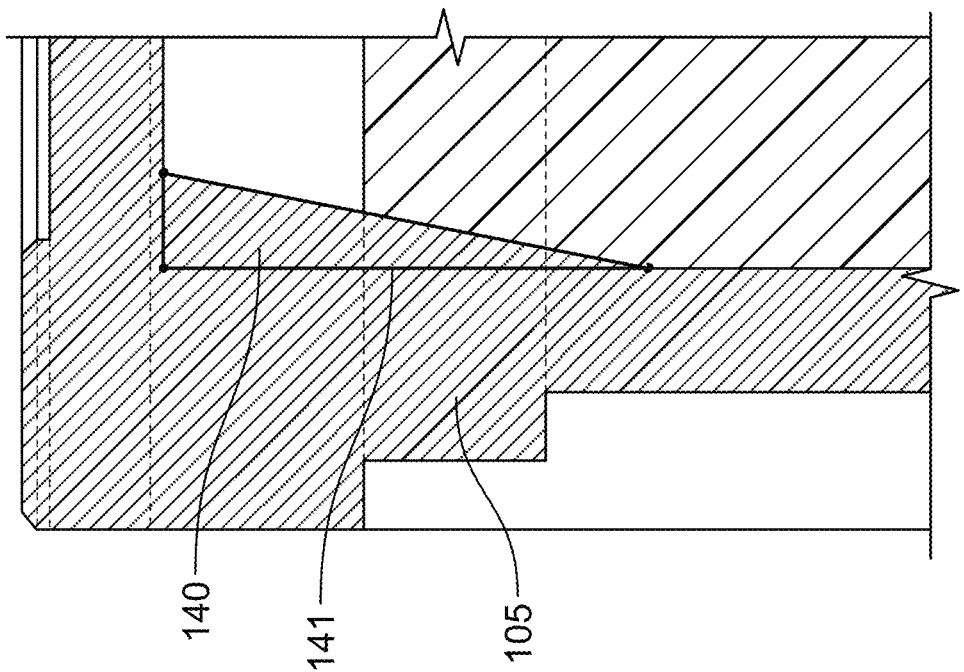
FIG. 10B
FIG. 10A

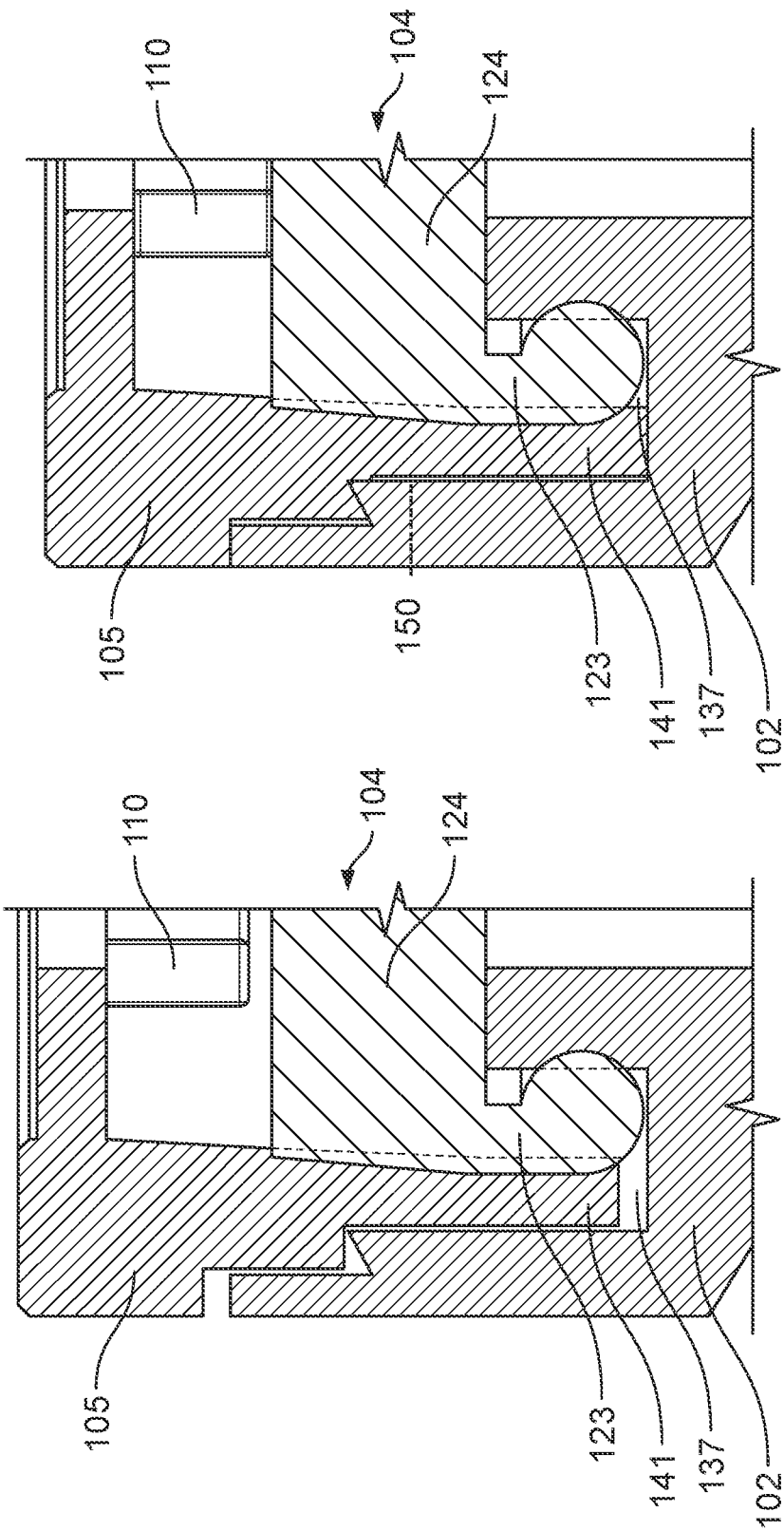

HEMOSTASIS VALVE FOR SHEATH ASSEMBLY

CROSS-REFERENCE TO RELATED APPLICATIONS

This application claims the benefit of the U.S. Provisional Application No. 62/935,300, which was filed on Nov. 14, 2019, and is incorporated by reference.

TECHNICAL FIELD

The present invention is directed to introducer sheath assemblies that permit the introduction of medical devices into a patient at an insertion site, such introducer sheath assemblies having a hemostasis valve to reduce or eliminate the discharge of body fluids from the patient through the insertion site of the introducer sheath assembly.

BACKGROUND

Patients with cardiac ailments are sometimes treated with heart pumps adapted to be inserted into the heart through adjoining blood vessels and configured to assist the natural cardiac pump function or to replace natural cardiac pump function by a continuous pumping operation.

In one common approach, an introducer sheath is used to gain vascular access prior to insertion of a medical device such as a heart pump. The introducer sheath is an assembly that includes a hemostasis valve that prevents blood leakage from the distal end of the introducer sheath upon insertion of the introducer sheath into a blood vessel. The hemostasis valve should prevent excessive blood leakage when no objects are present in the valve or when guidewires, catheters, blood pumps, or other objects are inserted through the valve. One of the primary causes of excess leakage in an introducer sheath is damage to or perforation of the hemostasis valve.

BRIEF SUMMARY

Described herein is an introducer sheath assembly for percutaneously delivering a medical device that maintains hemostasis in a patient. As illustrated, the sheath assembly has a sheath body and a sheath hub assembly coupled to the sheath body. The sheath hub assembly is a hub, a hub cap, a hemostasis valve and, optionally, foam. The hemostasis valve has a valve portion and a frame portion. The frame portion defines the perimeter of the valve and the frame portion has a thickness that is greater than the thickness of the valve portion, the valve portion having a plurality of offset slits formed through its thickness. The valve thickness is in the direction of travel of the medical device through the valve. The valve is formed from an incompressible elastomer.

Examples of the incompressible material are natural rubber, synthetic rubber, polyisoprene, polyurethane, silicone and a thermoplastic elastomer. Examples of thermoplastic elastomers are a Styrenic block copolymer and a thermoplastic vulcanizate.

Optionally, the hub has a valve seating feature formed therein. The valve seating feature is adapted to receive an extension of the frame portion of the valve and a seating portion of the hub cap. For example, the valve seat feature is configured as a channel having an inner wall with a first height and an outer wall with a second height, wherein the outer wall is higher than the inner wall. In this configuration, the valve portion sits above the inner wall of the valve seating feature and the extension of the frame portion of the valve extends into the valve seating feature.

Optionally, the seating portion of the hub cap, i.e. the portion of the hub cap that seats in the valve seating feature of the hub, is thicker at its proximal end than at its distal end. The hub cap is fixed into assembly with the hub and valve. Optionally, the hub cap portion is sonically welded to the hub portion.

Optionally, the hub has a flush port formed therein. Flush ports in such devices are well known to the skilled person and are not described in detail herein.

Optionally, the frame portion of the valve has an O-ring at the distal end of the extension from the valve portion. Optionally, the extension of the frame portion has a uniform thickness. In another optional configuration, the valve has frame extension portions that extend from both the proximal and distal sides of the valve body. In another configuration, the extension of the frame portion is an undercut extension.

The seating portion of the hub cap can be either straight or tapered. If the seating portion is tapered, that taper is either parallel or non-parallel to a tapered portion of the valve portion in contact with the seating portion as the hub cap is assembled to the valve and hub. If the seating portion is straight, it is either parallel or non-parallel to the valve portion of the valve portion in contact with the seating portion as the hub cap is assembled to the valve and hub.

Also described herein is a method for assembling an introducer sheath. In the method a hub with a valve seating feature formed therein is provided. Also provided is a valve with a valve portion and a frame portion, the frame portion being thicker than the valve portion. The valve is formed of an incompressible material having a plurality of helical slits formed in the valve portion. The frame portion extends beyond the valve portion. Also provided is a hub cap with a seating portion. According to the method the valve is assemble to the hub. At least a portion of the frame portion is received by the valve seating feature. The cap is assembled to the valve and hub such that at least a portion of the seating portion of the hub cap is received into the valve seating feature. The volume of the seating portion received into the valve seating portion causes the incompressible material in the valve seating feature to deform.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which:

FIGS. 8A-8D are photographs of the hemostasis valve according to a second embodiment before and after a guide wire is inserted therethrough;

FIGS. 10A-10B illustrate valve compression as the hub cap is assembled on the hub of the introducer assembly;

FIGS. 11A-11B illustrate the introducer assembly before and after the hub cap is ultrasonically welded to the hub;

DETAILED DESCRIPTION

Figure 1:
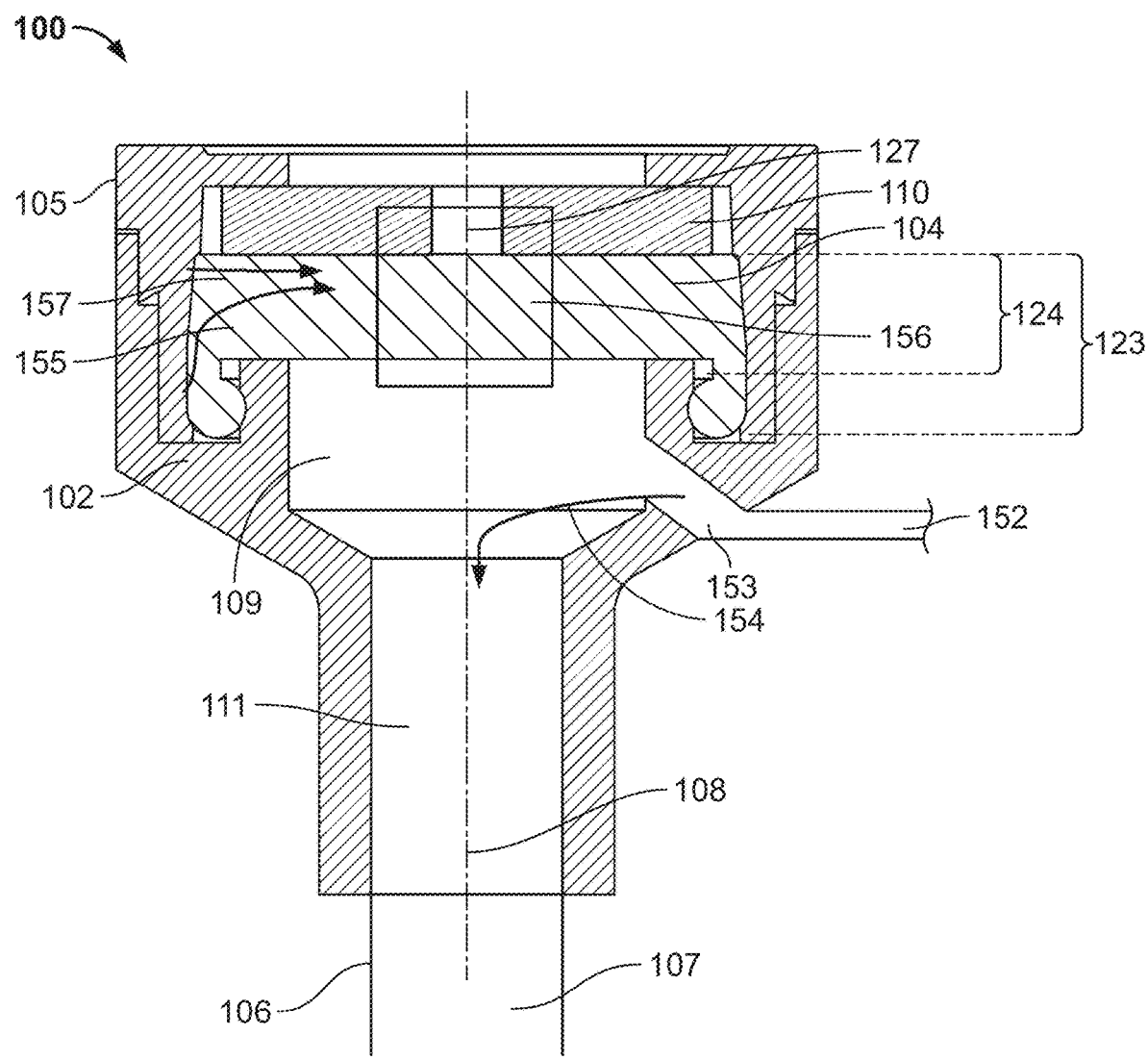
FIG. 1 illustrates a cross-section view of an introducer assembly having a hemostasis valve according to certain embodiments.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith.

The use of "/" in a FIG. or associated text is understood to mean "and/or" unless otherwise indicated. The recitation of a particular numerical value or value range or the use of terms such as approximately or about is understood to include or be a recitation of an approximate numerical value or value range (e.g., within +/−2%, +/−5%, +/−10%, +/−15%, or +/−20%).

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in An Introduction to Mathematical Reasoning: Numbers, Sets, and Functions, "Chapter 11: Properties of Finite Sets" (e.g., as indicated on p. 140), by Peter J. Eccles, Cambridge University Press (1998)). In general, an element of a set can include, be, or be a portion of a system, an apparatus, a device, a structure, an object, a process, a physical parameter, or a value depending upon the type of set under consideration.

As used herein, proximal is defined as toward or closer to the user, and distal is defined as further away from the user or in a direction away from or opposite to distal with respect to fluid flow. The term "vessel" is taken to mean an anatomical vessel, passage, or channel (e.g., a blood vessel, such as an artery) of a patient or subject, or an anatomical chamber or compartment. The term "perfusion" is taken to meant he injection, transfer, or communication of blood and/or one or more other fluids into a vessel for purpose of enabling the blood and/or other fluid(s) to reach an organ or tissues (e.g., to supply nutrients and oxygen thereto). The term "fluidically coupled" is taken to mean coupled in a manner that provides for fluid (e.g., liquid/gas) transfer or communication.

To provide an overall understanding of the systems, method, and devices described herein, certain illustrative embodiments will be described. Although the embodiments and features described herein are specifically described for use in connection with introducer sheaths and hemostasis valves for percutaneous insertion of heart pumps, it will be understood that all the components and other features outlined below may be combined with one another in any suitable manner and may be adapted and applied to other types of introducer sheaths and hemostatic valves or other types of cardiac assist devices, including balloon pumps.

The introducer sheath assembly described herein has a hub/hub cap/valve assembly wherein the geometry of the valve and the geometry of the hub cooperate to seal two fluid pathways thereby providing a hemostatic introducer sheath assembly. The fluid pathways independently sealed by the hub/hub cap/valve assembly are: 1) the fluid pathway around the valve between the valve and the hub or the hub cap; and 2) the fluid pathway through one or more slits in the valve that permit the insertion of a medical device/and mechanisms for introducing such medical device (e.g. a catheter; a dilator, etc.) through the slit or slits in the valve. The valve slits described herein cooperate with the hub/hub cap assembly to provide a hemostatic seal when closed and when a medical device is inserted therethrough.

The introducer sheath with the hemostatic valve and hemostatic hub/hub cap/valve assembly therefore provides two modes of sealing the valve, which is advantageous compared to prior art assemblies having only one mode of sealing (compression). As compression increases due to the seating of the hub cap within the hub, both modes of sealing increase. However, increasing compression increases the force needed to insert the device through the valve. Therefore, the amount of force exerted on the valve by the hub/hub cap assembly is controlled so that the insertion force required to pass devices through the slit remains within an acceptable range.

The valve is formed from an incompressible material such as silicone, natural or synthetic rubber, polyisoprene, polyurethane, and a thermoplastic elastomer. Other incompressible materials suitable for use in the present invention are well known to one skilled in the art and are not described in detail herein. The hub has volumetrically constrained structure referred to as a valve seat feature. The valve has a frame portion with an extension that will extend into the valve seat feature when the valve is seated in the hub. The hub cap has a seating portion that will also extend into the valve seat feature when the hub cap is assembled onto the hub. This arrangement provides a volumetric interference between the incompressible valve frame extension, the valve seat feature and the seating portion thereby providing a sealing pressure between the frame portion extension (e.g. an O-ring geometry) and the hub/hub cap. Because the incompressible valve frame extension fits within the valve seat feature, the volume of the incompressible valve frame extension is less than the volume of the valve seat feature into which it extends. When the seating portion of the hub cap is forced into the valve seat feature, this reduces the volume in the valve seating portion causing the incompressible valve frame extension to deform. This seals any potential fluid pathway between the valve and the hub/hub cap assembly.

The other fluid pathway sealed by the introducer sheath assembly described herein in the fluid pathway through the slits of the valve. The hub/valve/hub cap assembly are dimensioned to provide a radial interference between the hub cap and the valve portion of the valve that provides a sealing pressure on the surfaces of slits formed in the valve portion. This radial interference is provided by a taper geometry of the hub cap.

If the taper geometry of the hub cap is parallel to a corresponding taper on the valve, a substantially uniform compression along the thickness of the valve portion results. If the taper geometry is substantially non-parallel to a corresponding taper on the valve, a substantially non-uniform compression along the thickness of the valve portion results. In either example, the compression at the distal end of the valve is greater than at the proximal end of the valve.

Optionally, the hub cap has a straight geometry. In this option, if the straight geometry of the hub cap is substantially parallel to geometry of the valve, the compression along the length of the valve portion is substantially uniform. If the straight geometry is substantially non-parallel to geometry of the valve, a substantially uneven compression along the length of the valve portion results. In either instance the compression at the distal end of the valve is greater than the compression at the proximal end of the valve.

The systems, methods, and devices described herein thus reduce or eliminate the risk of bleeding that occurs during the insertion of medical devices (e.g., heart pumps), guidewires, dilators, or other objects. The hemostasis valve, and the manner in which it is disposed in the hub and hub cap, controls, reduces or prevents the loss of blood through the valve and around the valve.

Introducer sheath assemblies have two primary functions. First, the introducer sheath creates a pathway into desired vasculature to allow insertion and removal of devices. Second, any introducer sheath must maintain hemostasis throughout the access site through the entire insertion process. The hemostasis valve maintains hemostasis through the introducer sheath lumen. The hemostasis valve component is typically located in the most proximal portion of the introducer sheath known as the hub.

The hemostasis valve is required to form a seal when assembled into the hub. The hemostasis valve must maintain this seal when variable sized devices are inserted through it. As stated above, the hub and hub cap assembly exert forces on the hemostasis valve described herein to prevent fluid flow from the distal end of the sheath assembly through the proximal end (i.e. leakage from the sheath assembly insertion site).

For the valve to maintain its seal when devices are passed through it, the additional radial compression applied to the valve by the hub/hub cap assembly ensures that changes in the diameter of the inserted devices do not disrupt the seal. For the valve/hub/hub cap assembly described herein, this additional radial compression is provided by the placement of the valve into the hub cap. The hub and hub cap assembly are configured to operate on the elastomeric valve to provide the requisite valve compression. The valve has a descending sidewall thickness that cooperates with the hub cap fitted within the hub to form the desired seal. Optionally, the descending sidewall of the valve terminates in an O-ring. The insertion of the hub cap downward into the hub exerts a compressive force on the slitted valve to seal the valve. Optionally, the hub cap has an opening that is tapered such the diameter of the hub cap interior that receives the valve reduces as the hub cap advances further into the hub. This tapered diameter is referred to as a compression feature herein.

For an introducer sheath to be compatible with the devices that have multiple diameters, such as the blood pumps described herein, a seal must be formed with devices that have a variety of diameters such as 9 French (3 mm), 10 French (3.33 mm), 11 French (3.67 mm), 12 French (4 mm), 13 French (4.33 mm), 14 French (4.67 mm), 15 French (5 mm), 16 French (5.33 mm), 17 French (5.67 mm), 18 French (6 mm), 19 French (6.33 mm), 20 French (6.67 mm), 21 French (7 mm), or any other suitable diameter. Blood pump devices that can be inserted through the introducer sheath assembly described herein are described in, for example, U.S. Pat. No. 7,736,296 entitled, "Intercardiac Blood Pump" to Seiss et al., which is incorporated by reference herein.

For blood pump insertion, the valve must be capable of maintaining a seal under the following conditions:
i) Sheath only (when there is nothing in the valve);
ii) Dilator only inserted in the valve (the dilator can be silicone coated and inserted into the valve to lubricate the valve prior to inserting the pump device through the valve);
iii) A first guidewire inserted in the valve (e.g. a 0.035" (0.889 mm) diameter guidewire will be passed through the hemostasis valve and used to advance the pump through the valve);
iv) A 6 Fr guide catheter inserted through the valve;
v) A second guidewire inserted in the valve (e.g. a 0.018" (0.457 mm) diameter guidewire);
vi) The second guidewire in v) but inserted in the valve along with the 9 Fr catheter portion (3 mm) of the pump; and
vii) The pump device (9 Fr (3 mm) catheter portion).

The above conditions are listed by way of example and are not limiting. The assembly described herein solves the hemostasis and minimal insertion and removal force problems as well as maintaining ease of manufacture in the hub, hub cap, and valve itself. The assembly described herein provides hemostasis for each of the variable sized devices inserted through the valve. The seal is also maintained when such devices are removed.

Figure 12:
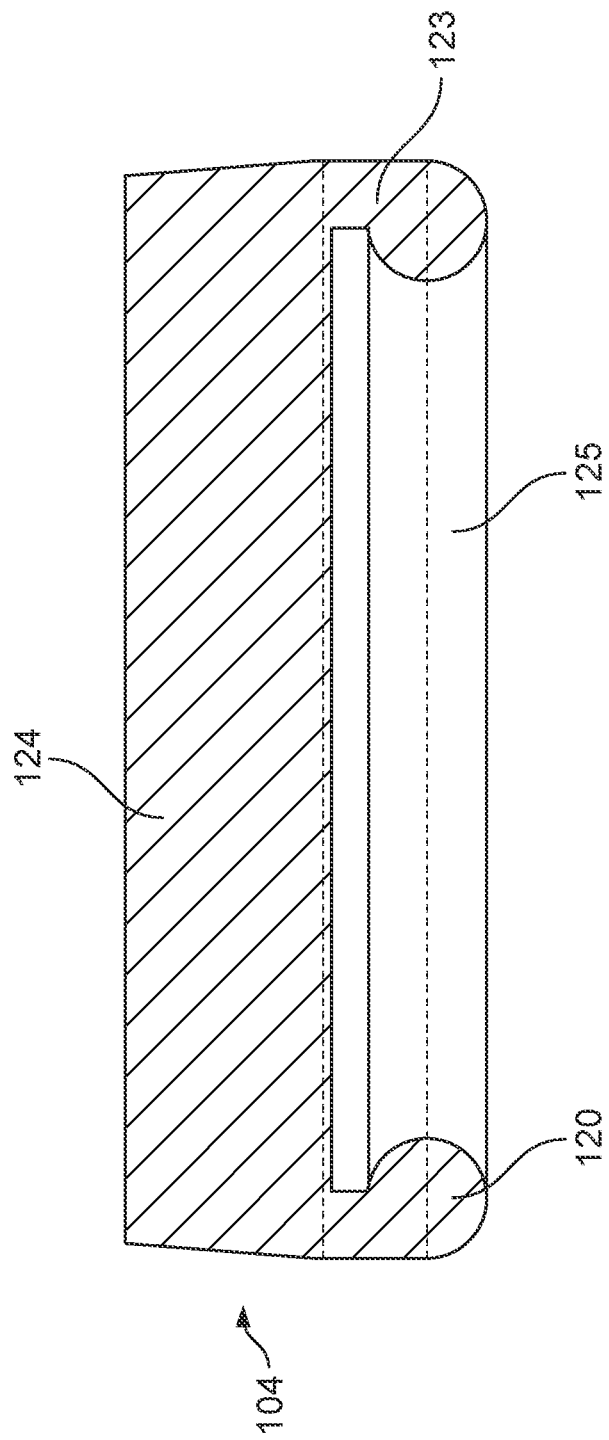
FIG. 12 is a cross section view of the hemostasis valve illustrated in FIG. 6.

The valve described herein is structured as a thin (e.g. about 2 mm to about 4 mm) disc that is received into the hub/hub cap assembly. The valve is circular because the hub/hub cap assembly defines an internal lumen with circular cross section through which the devices are inserted into the patient. The valve is made of soft silicone or a flexible polymer such as natural or synthetic rubbers, polyisoprene, polyurethane, or a thermoplastic elastomer like Styrenic block copolymers or thermoplastic vulcanizate. The disc has first and second thicknesses. The first perimeter thickness is greater than the second interior thickness. The thicker perimeter portion of the disc is referred to as the frame portion and the thinner interior portion is referred to as the valve portion. The first thickness is therefore referred to herein as the frame thickness and the second thickness is referred to as the valve thickness. Both thicknesses are in the axial direction of the introducer sheath assembly. Referring to FIG. 12, the valve 104, shown in section view, has a frame portion 123 illustrated in FIG. 1 that terminates as O-ring portion 120 extending from the frame portion 123 above the O-ring portion 120. The valve 104 has a valve portion 124 that is thinner than the frame portion 123. The O-ring is made of an incompressible material such as the materials described elsewhere herein. The O-ring portion 120 defines an inner and outer circumference over which the thinner valve portion 124 extends. The interior void portion is designated 125. The O-ring 120 is optional as described elsewhere herein. As described herein, the O-ring 120 is one example of the incompressible features described herein.

FIG. 1 is a cross-section view of an introducer sheath assembly 100 including a hemostasis valve 104 disposed in a hub 102, having a hub cap 105 assembled thereto. The hub has an inner cavity 109 that receives the hemostasis valve 104 and tapers to an inner lumen 111. The hemostasis valve has a valve portion 124 that is thinner than the frame portion 123. The hub 102 is also assembled to elongate introducer body 106 (i.e. the sheath) that has an inner lumen 107 and a longitudinal axis 108. The inner lumen 111 of the hub is fluidically coupled to the inner lumen 107 of the elongate introducer body. The introducer assembly optionally includes a lubricating foam 110. The lubricating foam actively lubricates devices inserted therethrough. Suitable lubricating foams are well known to one skilled in the art and not described in detail herein. Optionally, the lubricating foam 110 is an open-cell polyurethane that absorbs and holds a lubricating liquid, such as silicone oil. The foam 110 has attachment features to the cap to hold it in place. Such attachment features are known and are therefore not illustrated herein. The foam 110 has a through hole 127 to pass devices so that they are passively lubricated by the silicone oil in the open cell network. Optionally, the foam may be provided in portions and assembled with the valve 104 as the hub cap 105 is placed thereover.

The hub 102 has an inlet 153 (i.e. a flush port) that fluidically couples fluid supply line 152 to the inner lumen 111 of the hub 102. Arrow 154 indicates the flow path for the fluid entering the hub 102 through the inlet 153. When the hub cap 105 is fully seated into hub 102, the hub cap 105 and hub 102 combine to deform the O-ring (since the O-ring is incompressible, its volume does not change). This force 155 seals potential fluid pathways in a valve region 156 between the valve 104 and the hub 102/hub cap 105. The hub cap 105 also exerts a compressive force 157 on the valve 104. Compressive force 157 seals the valve 104 in the hub 102/hub cap 105 so that there is no fluid flow from the inner lumen 111 of the hub 102 back through the valve 104. The frame portion 123 of valve 104 terminates in an O-ring 120 as illustrated in FIG. 1. FIG. 1 illustrates O-ring 120 in an undeformed state, illustrating the change in dimension of the valve 104 and its O-ring portion 120 caused by full seating of the hub cap 105 on the hub 102.

Figure 2:
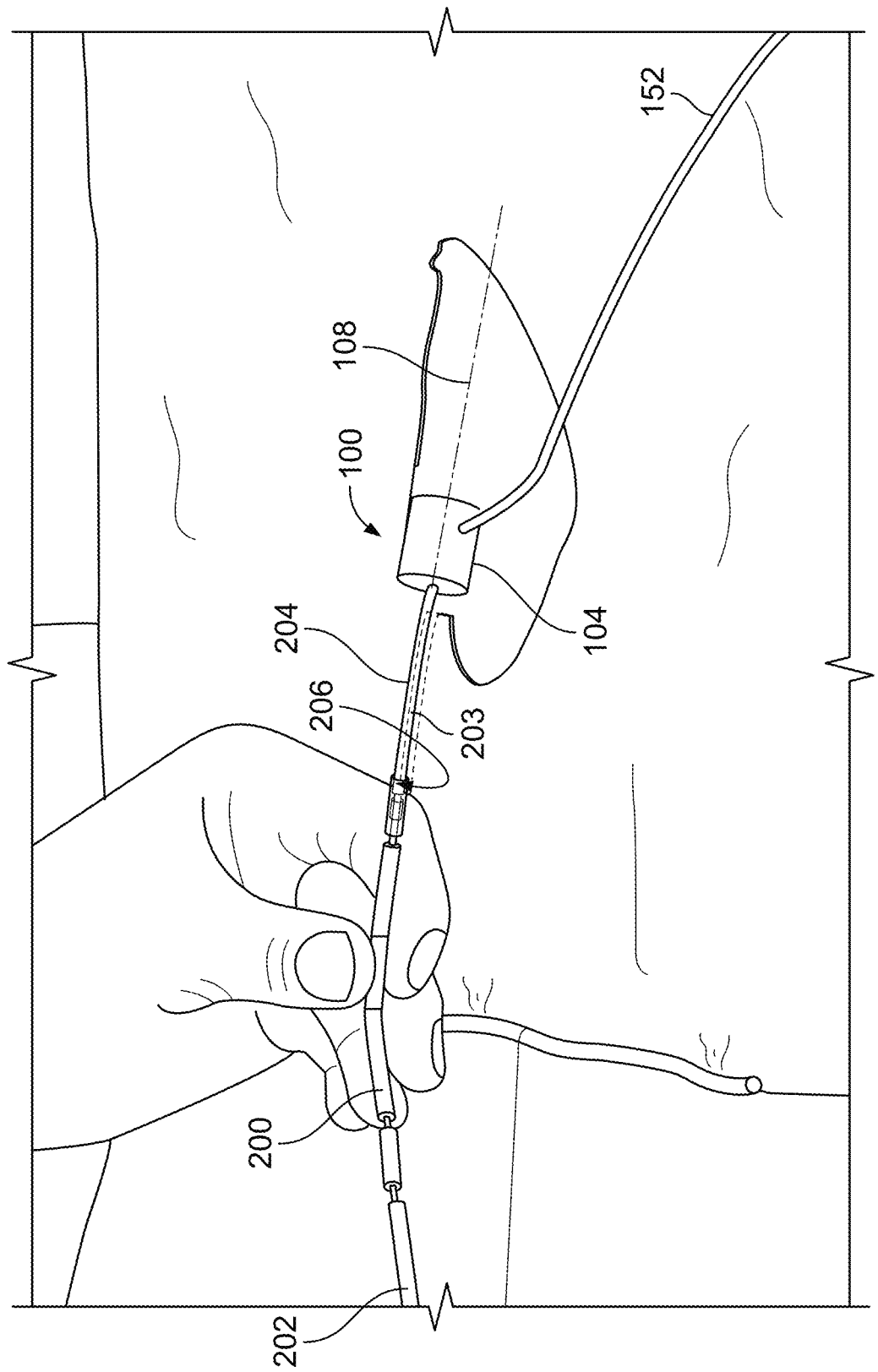
FIG. 2 shows percutaneous insertion of a heart pump using an introducer assembly that deploys the hemostasis valve of FIGS. 1 and 2.

FIG. 2 shows percutaneous insertion of a heart pump assembly 200 using an introducer sheath assembly 100 that carries the hemostasis valve 104 of FIG. 1. The heart pump assembly 200 includes a distal end portion 203 including outlet 206 and a supply catheter 202. The introducer sheath assembly 100 is illustrated as an assembly that also includes the fluid supply line 152 for the flush port 153. The fluid supply line has a valve (not shown) that is used to turn the flow of fluid into the introducer sheath assembly on and off. The fluid supply line 152 may be used to flush the introducer sheath assembly 100 before during or after insertion of the heart pump assembly 200. The distal end portion 203 of the heart pump assembly 200 is inserted into the introducer sheath assembly 100 along an insertion path 204

Figure 3:
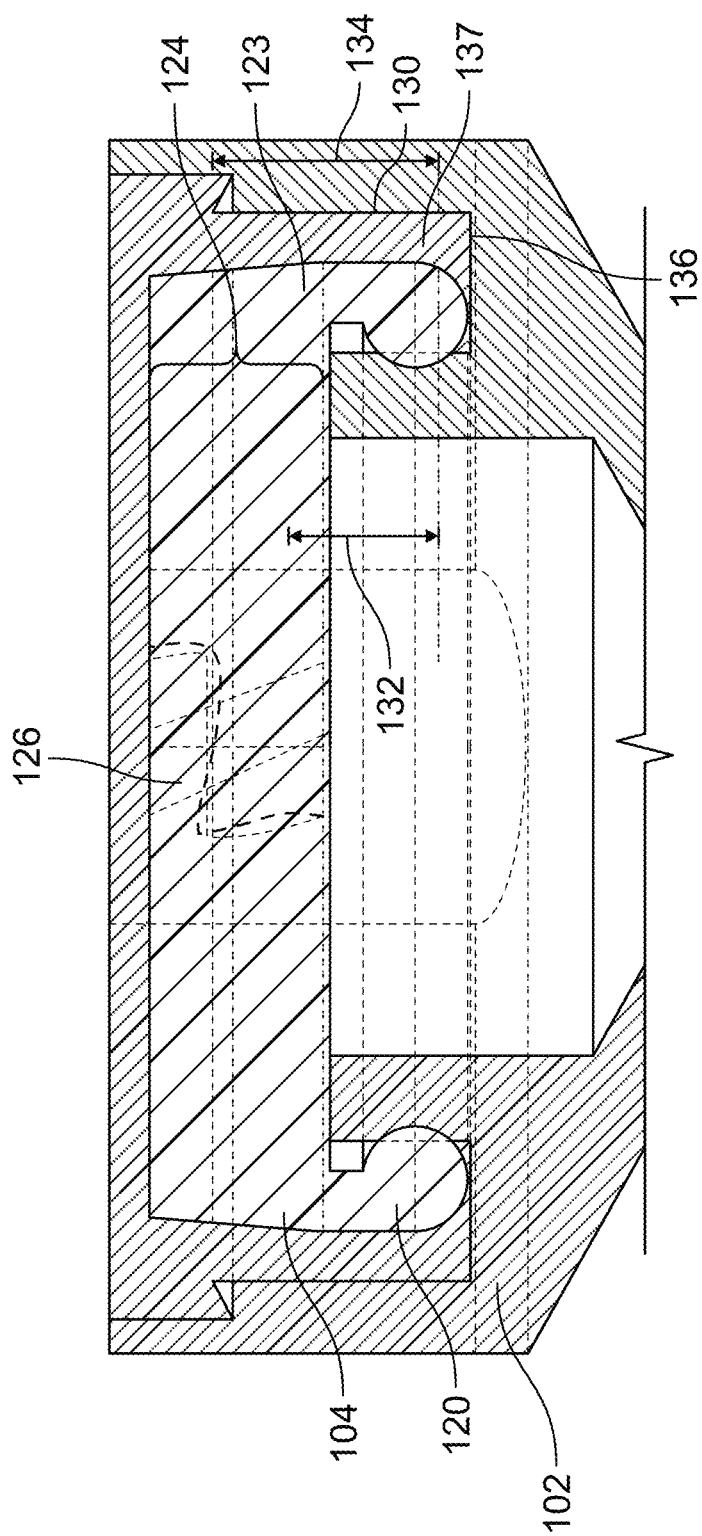
FIG. 3 is a detailed cross-section of the hemostasis valve seated in the hub.

FIG. 3, illustrates a helix slit 126 formed through the thickness of the valve portion 124 of the valve 104. Such slits are described in WO2019090351 to Korkuch et al., which is commonly owned with the present application. WO2019090351 is incorporated by reference herein. A helix slit, as used herein, is a slit in which the cuts in the material are offset through the thickness of the valve portion. For example, the helix slit 126 may form a spiral through the thickness of the valve portion. The cut may be one cut or a plurality of cuts. Such slits are well known to those skilled in the art and are not described in detail herein.

Figure 5:
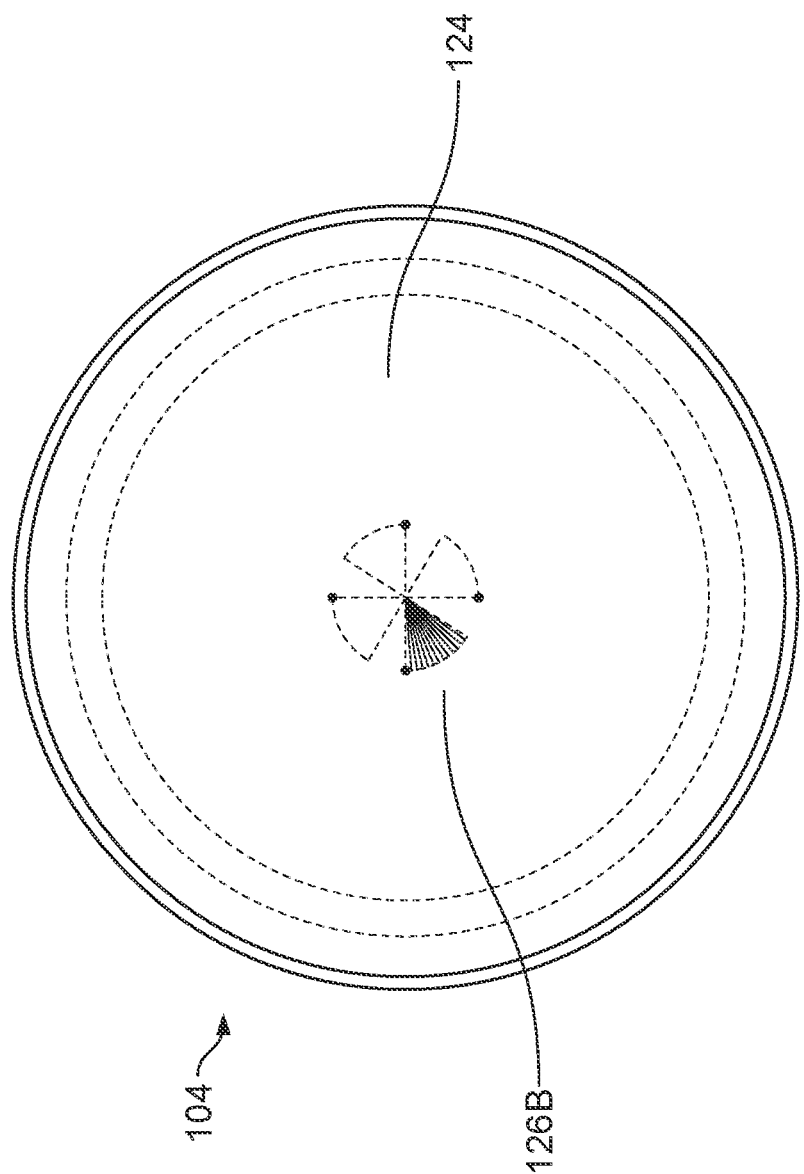
FIG. 5 is a bottom view of the hemostasis valve according to second embodiment.

The helical slits 126 traverse through the center of the valve through the thickness of the valve portion 124. The helical slits 126 follow a spiral path through the valve portion 124 thickness from the lines 126A on the top surface of the valve 104 (FIG. 6) to the lines 126 B on the bottom surface of the valve (FIG. 5). The length of the first group of lines 126A and the second group of lines 126B determines the size of the helical slits 126. The size of the helical slits 126 may be set to balance the hemostasis performance with the insertion and removal force of the medical devices inserted through the hemostasis valve 104. As the length of the first group of lines 126A and the second group of lines 126B increases, the size of the helical slits 126 increases, the hemostasis performance of the hemostasis valve 104 decreases, and the removal force of the medical devices inserted through the hemostasis valve 104 also decreases.

Figure 4:
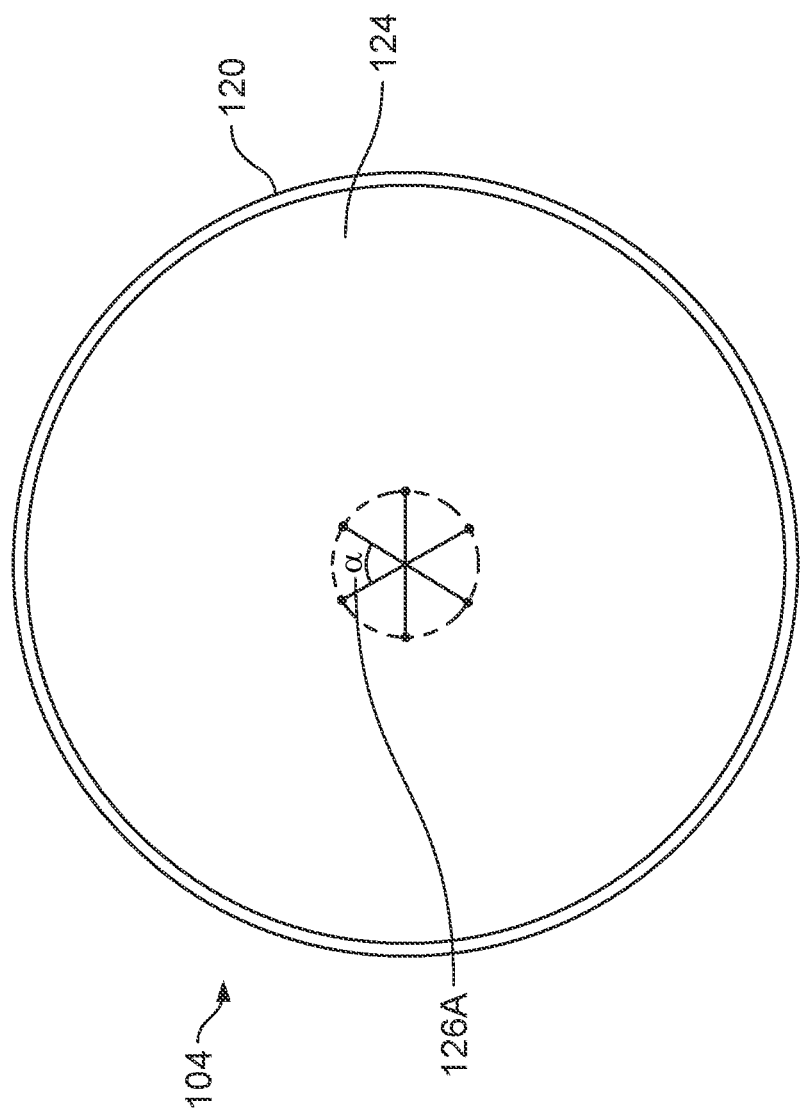
FIG. 4 is a top view of the hemostasis valve according to one embodiment.
Figure 6:
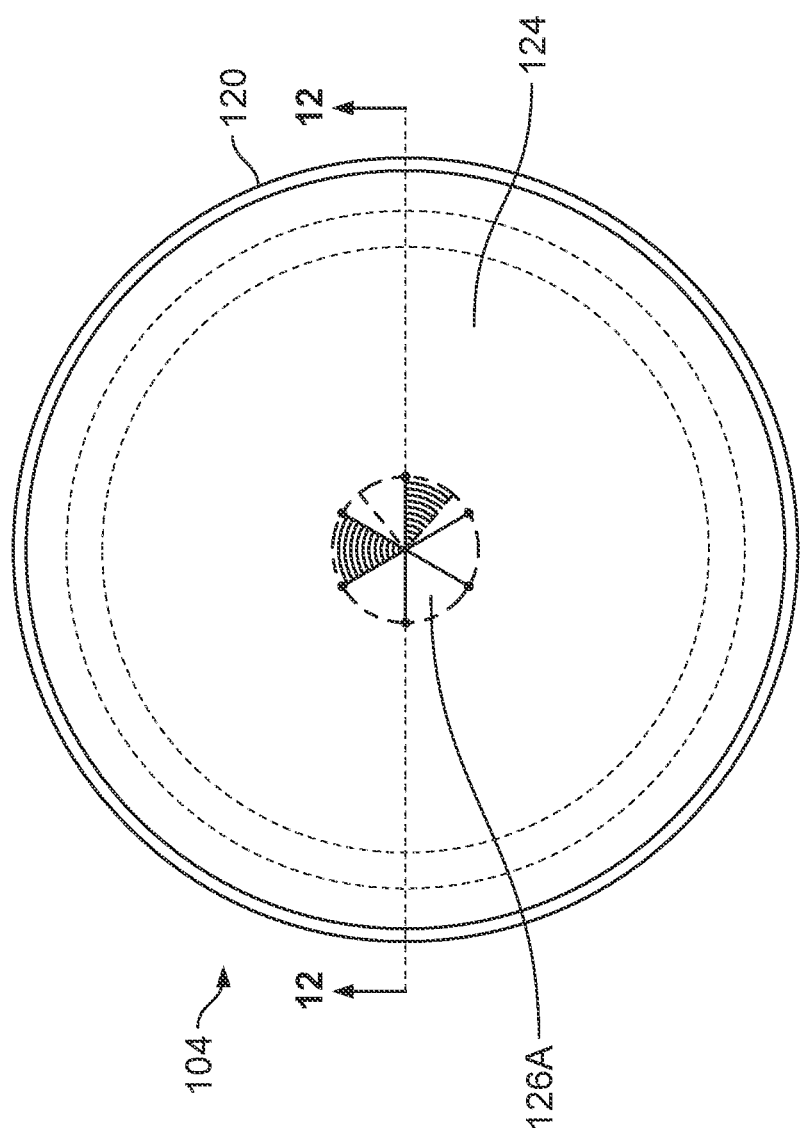
FIG. 6 is a top view of the hemostasis valve of FIG. 4.

As depicted in FIG. 4, the angle α of the helical slits 126 defines an angular path the helix slits 126 go through as they traverse the valve 104 through its thickness. In general, a can be any angle that matches the angular offset between the first group of lines 126A on the top surface of the valve portion 124 and the second group of lines 126B on the bottom surface of the valve portion 124. In another aspect, the angle α matches the angular offset of two of the helical slits 126 on the top surface of the valve portion 124. In some aspects, a is equal to 360/n, where n is a number of helical slits 126. In another aspect, a is not related to the angular offset of two of the lines 126A on the top surface of the valve portion. In this case, a is the angle of rotation of the helix between the top surface and the bottom surface of the valve portion 124, and need not correspond to an angle between two lines 126A, such that the first group of lines 126A and the second group of lines 126B may be angularly offset from each other. This is illustrated in FIG. 6.

The valve 104 is illustrated as being received within hub 102. The hub 102 defines a groove or channel 136 that receives the frame portion 123 of the valve 104, including, as illustrated in FIG. 3, the O-ring 120 of the valve 104. The channel 136 forms a valve seat feature 137 that has an inner channel wall height 132 and an outer channel wall height 134. The valve portion 124 is supported in the hub 102 by the inner channel wall 130. To assemble the hub 102, valve 104 and hub cap 105, the valve 104 is first placed in the hub 102. The O-ring 120 stretches slightly over the inner channel wall 132 as it is received in the valve seat feature 137 in the hub 102. However, the O-ring 120 is not compressed when inserted into the hub 102. Potential leakage of fluid through the distal end of the introducer sheath assembly is reduced or eliminated by joining the hub cap 105 to the hub 102.

As noted above, the incompressible feature 120 (e.g. O-ring) is the frame portion 123 that extends from the valve portion 124. The frame portion has an inner circumference and an outer circumference and is received by the valve seat feature 137. The inner diameter of the valve seat feature 137 is larger than the diameter of the inner lumen 111. Since the incompressible portion is received within the valve seat feature 137 and the inner diameter defined by the incompressible feature 120 is larger than the inner lumen, the incompressible feature 120 does not contact or otherwise engage with devices that pass through the helix slit 126 and the inner lumen 111 of the introducer sheath assembly 100.

FIG. 4 is a top view of the valve 104 in which the valve portion 124 has the helix slit 126A, illustrated as a series of offset cuts, disposed therein. The O-ring 120 is disposed beneath the valve portion 124 but has both inner and outer diameters that extend beyond the outer diameter of the valve portion 124. The valve 104 can be formed as a monolithic article by injection molding or other molding techniques, making the design and configuration of the valve reproducible within very close tolerances. When a device (not shown) is passed through the first group of lines 126A (i.e. the helical slit), hemostasis is achieved through the helical slit/cut design in addition to the radial compression of the valve 104 by the hub 102 and hubcap 105 of the introducer sheath assembly 100.

FIG. 5 is a top down view of the valve 104. The valve telescopes in slightly from the O-ring 120 upward to the valve portion 124 into which the second group of lines 126B (i.e. the helical slit) is formed. FIG. 5 illustrates an optional valve slit 126 configuration that changes from the 3-cut helix to a 2-cut configuration. Although a helix is not reflected in the 2-cut configuration, the helix does propagate through the thickness of the valve portion 124.

The hemostasis valve 104 is optionally made of soft silicone. Durometers of 20A, 30A and 40A (i.e. Shore A hardness) are contemplated as suitable. The valve could also be made of a completely different elastomer that exhibits similar characteristics such as a lower durometer hardness. Examples of such materials are natural or synthetic rubbers, polyisoprene, polyurethane, or a thermoplastic elastomer like Styrenic block copolymers or thermoplastic vulcanizate. Optionally, the hemostasis valve 104 is made of a medical grade silicone or other elastomer.

FIG. 6 is the valve of FIG. 4 but with the helical cuts illustrated as the cuts progress through the valve portion 124. FIG. 6 also illustrates that the diameter of the valve portion tapers inward slightly from its distal end to its proximal end. The cross section of the valve illustrated in FIG. 6 along line 12-12 is illustrated in FIG. 12.

Figure 7A:
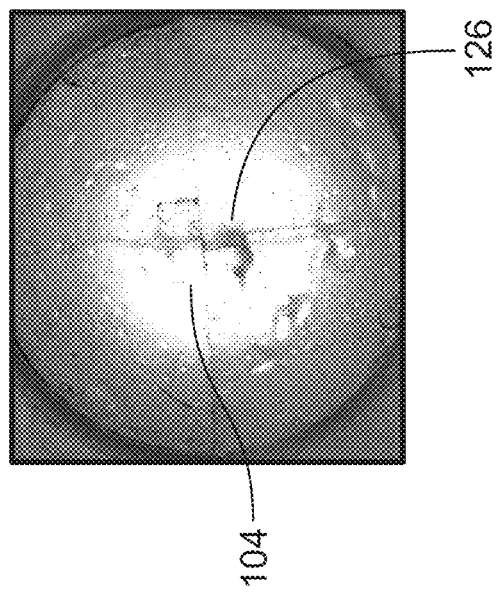
FIGS. 7A-7C are photographs of the hemostasis valve according to a first embodiment before and after a guide wire is inserted therethrough.
Figure 7B:
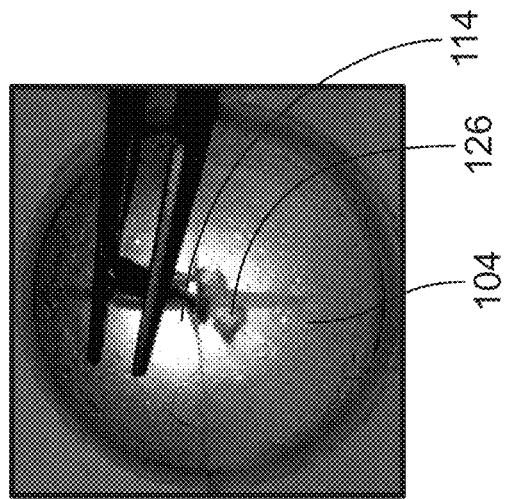
Figure 7C:
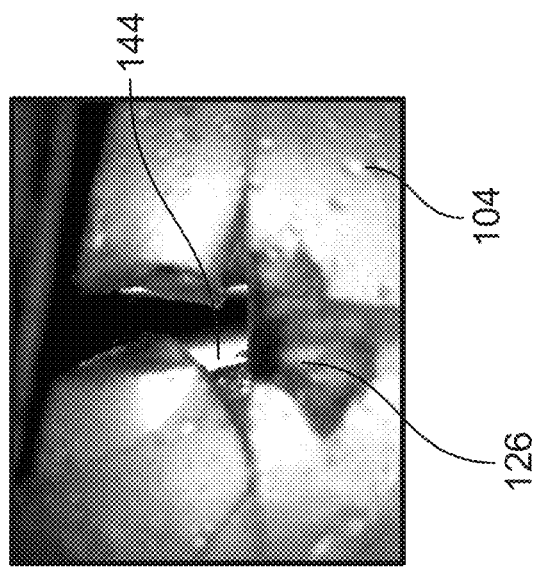

FIGS. 7A-C are photographs of the hemostasis valve 104 with the helical slit 126 formed in an x-pattern. FIG. 7A is the valve 104 before anything has been inserted through the slit 126. FIG. 7B is the valve 104 after a guidewire 114 has been inserted through the valve 104. FIG. 7C is a close-up view of the slit 126 that has been disrupted by the guidewire 114. It should be noted that, in FIG. 7B, there is gap 144 through the valve 104 that forms when the guidewire 114 is pulled slightly off center. Typically, a device inserted after the guidewire 114 has been successfully passed through the introducer sheath assembly 100. FIG. 7C is a magnified view of the gap 144 formed in the valve depicted in FIG. 7B.

FIGS. 8A-D are photographs of the hemostasis valve 104 with the helical slit 126. The helical slit is propagated through the thickness of the valve portion 124 of the hemostasis valve 104. The slit 126 in the valve in FIG. 8B has been pushed through to reveal the helical nature of the helix slit 126 (i.e., the cuts are offset as the cuts advance through the thickness of the valve portion 124). FIG. 8C is an image of the valve 104 with the guidewire 114 through the slit 126. FIG. 8D is the valve 104 when the guidewire 114 through the slit 126 is pulled off center.

Figure 9:
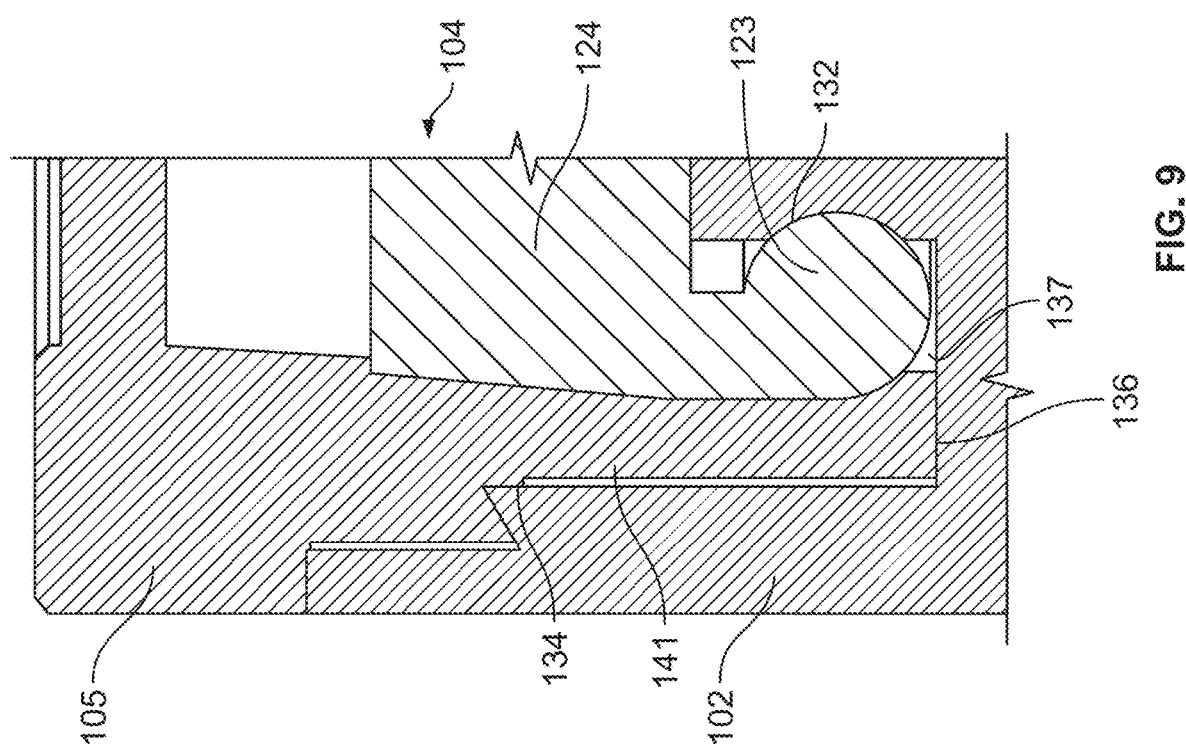
FIG. 9 is a detailed view of a portion of the introducer assembly of FIG. 1.

Referring to FIG. 9, there is detailed cross-section of the introducer sheath assembly 100 in which the hub cap 105 is mated with the hub 102 thereby compressing the frame portion 123 of the hemostasis valve 104 in the valve seat feature 137. The hub cap 105 has a seating portion 141 that is pushed into the valve seat feature 137 between the inner wall 132 and the outer wall 134 of the channel 136 in hub 102. The relaxed state of the O-ring portion 120 is illustrated in phantom in FIG. 9. Since the O-ring portion 120 is made of an incompressible material, the available volume for the O-ring in the valve seat feature 137 is reduced when the seating portion 141 of the hub cap 105 placed therein. The reduced volume causes the O-ring portion 120 to exert forces that substantially seal fluid pathways between the valve, hub and hub cap.

Figure 17:
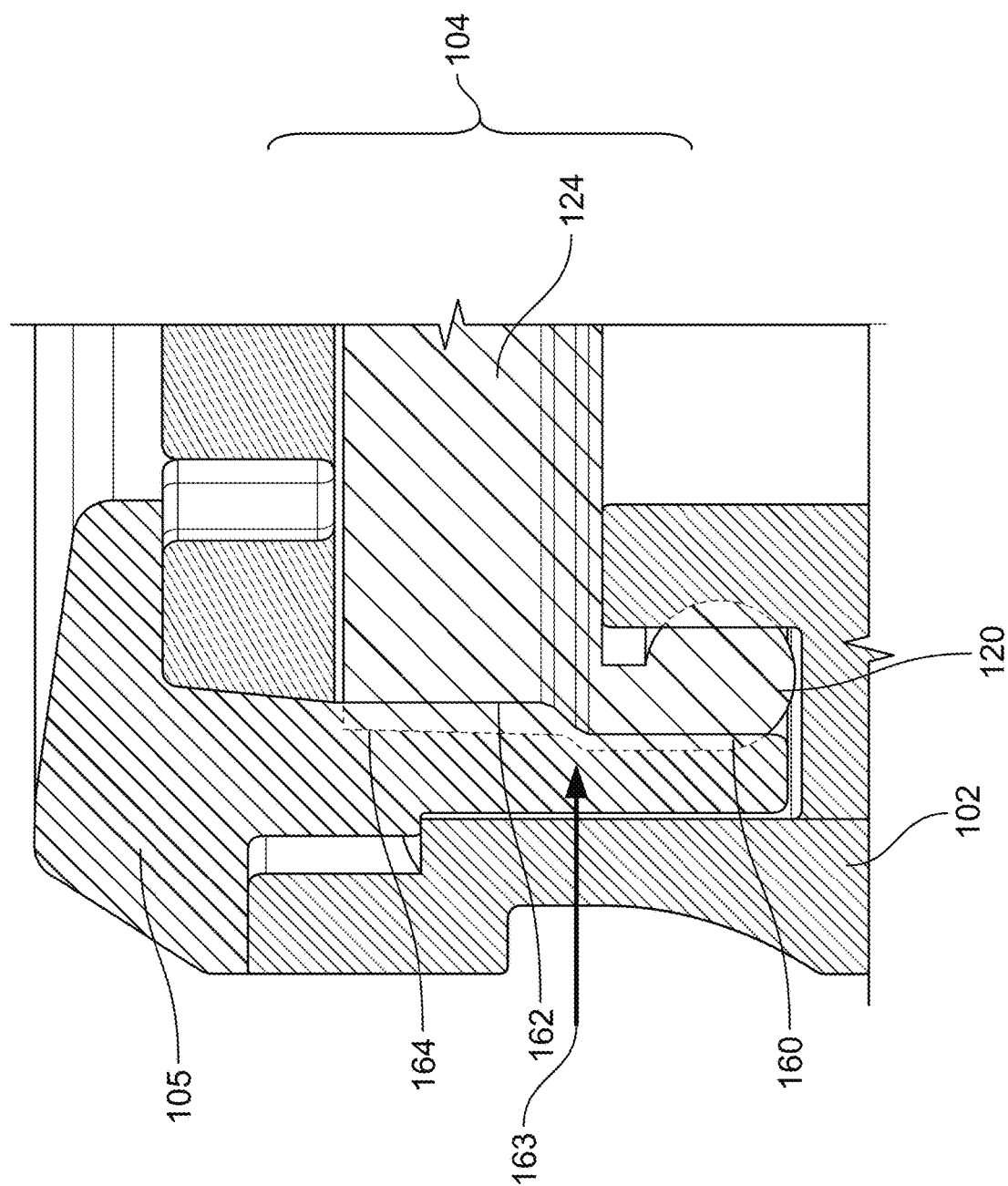
FIG. 17 is an illustration of an alternative configuration of the hub cap that exerts pressure in two regions.

Referring to FIG. 17, the hub cap 105 has a stepped inside portion that provides targeted lateral deformation to the valve portion 124 and the O-ring portion 120. As the hub cap 105 is seated onto the hub 102, stepped portion 160 is sized to exert lateral force 163 onto the O-ring 120. Stepped portion 162 is sized to exert lateral force 163 onto the valve portion 124 (which has a laterally recessed vertical perimeter profile with respect to the vertical perimeter profile for the O-ring 120). Illustrated in phantom 164 is the profile of the valve portion 124 and the O-ring 120 prior to deformation by the stepped portions 162 and 160, respectively. When the hub cap 105 is fully seated onto the hub 102, the stepped portions conform to the strictures imposed by the stepped portions 160, 162 of the hub cap 105.

Referring to FIGS. 10A-B, the hub cap 105 is illustrated as having a compression feature 140. The cap 105 with the compression feature 140 is illustrated in FIG. 10A. The compression feature 140 is illustrated as a surface that tapers inwardly and downwardly in the portion of the hub cap 105 into which the valve portion 124 of the valve 104 is received. This compression feature 140 seals the slits in the valve portion 124 through the thickness of the valve portion 124. Optionally, the compression feature can be straight. If the compression feature is straight, the slits are sealed across the lateral extent of the valve portion 124. As can be seen from line 142 in FIG. 10B, the frame portion 123 of the valve 104 has been compressed inwardly by the compression feature 140. As stated above, this compression feature mitigates leakage from the distal end of the introducer sheath assembly 100 that might otherwise occur through the slits in the valve 104. As noted above, the introducer sheath assembly described herein mitigates leakage through two different pathways, one pathway being through the valve 104 and the other being a pathway around the valve 104.

The progression of the hub cap 105 into the hub 102 for engagement therebetween is illustrated in FIGS. 11A-B. In FIGS. 11A-B the valve profile prior to hup cap placement in the hub is illustrated in solid lines and the profile after hub cap insertion is in dashed lines. Referring to FIG. 11A, the hub cap 105 sits above the hub 102 and the valve 104, which is placed in the hub 102 prior to the hub cap 105 being placed thereover. The valve has thinner valve portion 124 and thicker frame portion 123. The valve O-ring 120 rests in valve seat feature 137. Extending downward from the hub-cap 105 is foam 110. The seating portion 141 of hub cap 105 extends into the valve seat feature 137.

Referring to FIG. 11B, the hub cap 105 and hub 102 are urged into contact with each other. As noted above, urging the hub cap 105 into the valve seat feature 137 deforms the incompressible the O-ring 120 which, in turn, seals any potential liquid pathways between the valve 104 and the hub 102/hub cap 105. The valve portion 124 stretches slightly over the valve seat feature 137 in the hub 102, but is not compressed until the seating portion 141 of the hub cap 105 is urged downwardly onto the hub 102. The seating portion of the hub cap 105 compresses the O-ring 120 in the valve seat feature 137 of the hub 102. The O-ring 120 is not fully compressed until the hub cap 105 is fully seated on the hub (e.g., the hub cap 105 is ultrasonically welded to the hub 102). The ultrasonic weld is illustrated as 150 in FIG. 11B.

The foam 110 in the hub cap 105 can be formed as pins (not shown) that assists in the engagement of the hub cap 105 with the valve 104. The valve 104 is either formed from silicone or coated therewith to reduce any frictional force or insertion force between the valve 104 and the device(s) inserted therethrough.

FIG. 12 is a cut away view of the valve 104 illustrated in FIG. 6. illustrates a section of the valve 104 from the perspective of the valve interior, such that a portion of the O-ring 120 is visible along with the valve portion 124 above the O-ring. The void 125 is the portion of the valve interior defined by the frame portion 123 and the valve portion 124.

Figure 13:
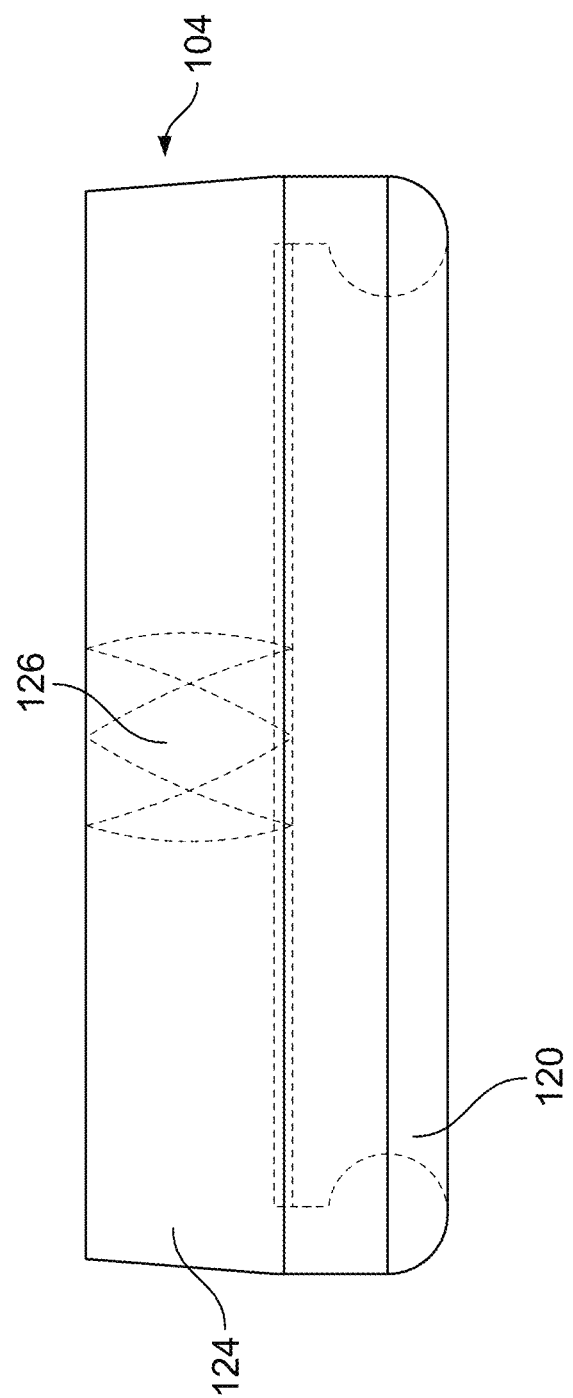
FIG. 13 is a section view of the interior perimeter of the hemostasis valve of FIG. 12.

FIG. 13 is a side view of the hemostasis valve 104 in FIG. 12. In this view, from the outer perimeter of the valve, the O-ring 120 is shown in phantom, since it is located in the interior perimeter of the valve portion. The helix slit 126 is also shown in phantom. The helix slit 126 is formed through the thickness of the valve portion 124.

Figure 14:
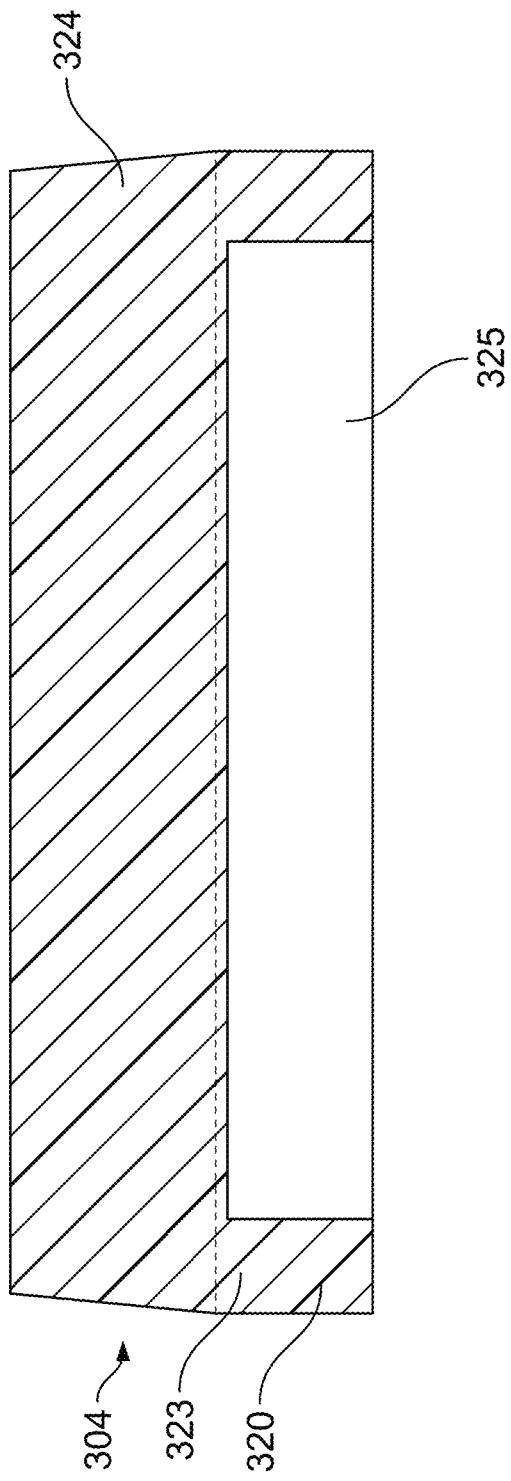
FIG. 14 is a section view of the exterior perimeter of the hemostasis valve according to a second embodiment.

FIG. 14 is an alternative hemostasis valve configuration, 304, also shown in cross-section, like FIG. 12. In this configuration, the O-ring is replaced by a straight extension 320 of the frame portion 323 of the valve 304. In this example, extension 320 is the incompressible feature that will be subjected to compressive force in the valve seat feature 137 when the hub cap 105 is assembled to the hub 102. The valve portion 324 has the helical slit (not shown) formed therethrough. The extension 320 extends below valve portion 324 and otherwise performs the functions of the O-ring described in prior embodiments. The frame portion 323 and the valve portion 324 define the void 325 under the valve portion 324.

Figure 15:
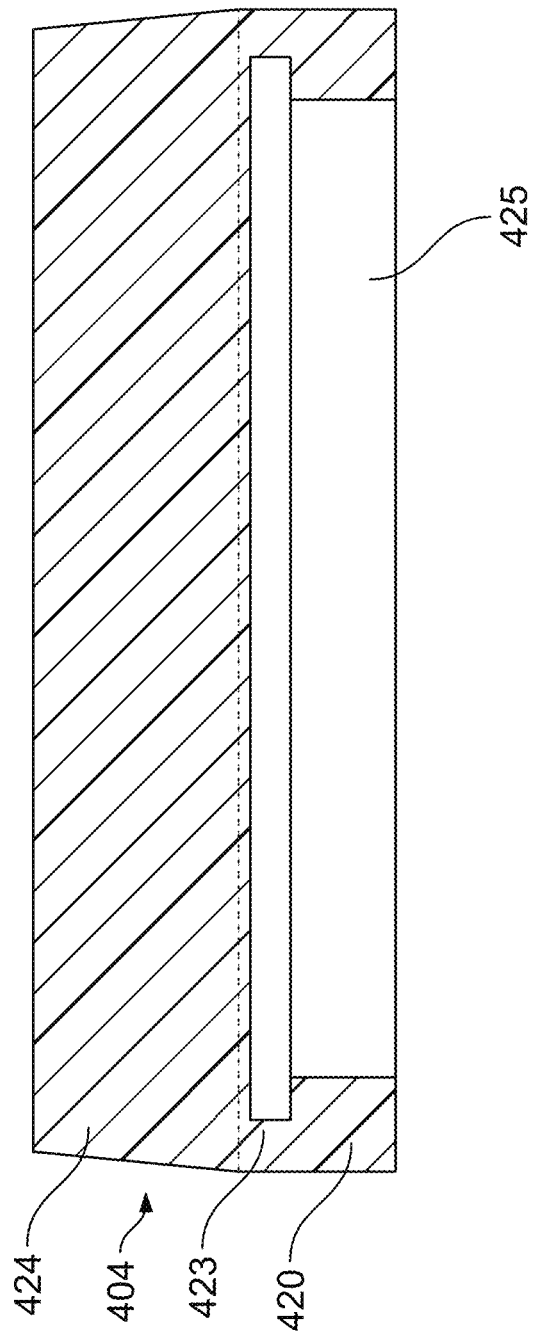
FIG. 15 is a section view of the exterior perimeter of the hemostasis valve according to a third embodiment.

FIG. 15 is an alternative hemostasis valve configuration, 404. In this configuration, the O-ring is replaced by an extension 420 of the frame portion 423 that is squared off instead of a round O-ring structure. The undercut extension 420 will also be received by the valve seat feature of the hub (not illustrated in FIG. 14) and is the incompressible feature of valve 404. The valve portion 424 still has the helical slit (not shown) formed therethrough. The frame portion 423 and the valve portion 424 define the void 425 under the valve portion 424.

Figure 16:
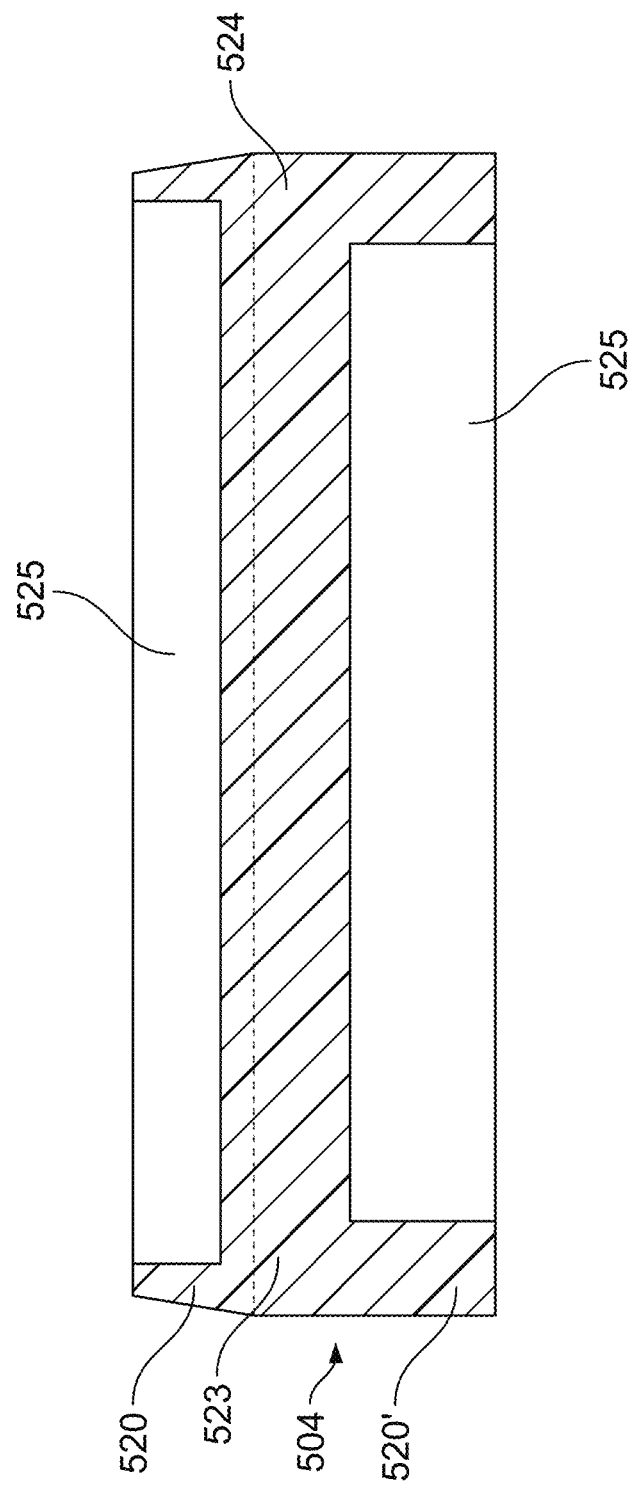
FIG. 16 is a section view of the exterior perimeter of the hemostasis valve according to a fourth embodiment.

FIG. 16 is an alternative hemostasis valve configuration 504. This hemostasis valve 504 has a frame portion 523 with two extended portions 520 and 520'. Incompressible feature 520' is received by the valve seat feature while 520 also anchors the hemostasis valve 504 in the introducer sheath assembly when devices are removed therefrom. The helical slit is formed in the valve portion 524 that is intermediate the two extensions 520 and 520' of the frame portion 523 of the valve 504. The valve 504 has two voids defined by the valve portion 524 and the frame portion 523. One void 525 is above the valve portion 524 and the other void 525 is below the valve portion 524

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. It is to be understood that the introducer assembly described herein may be applied to other systems in which access to an arteriotomy of a patient is desired while preserving hemostasis. Variations and modifications will occur to those of skill in the art after reviewing this disclosure. The disclosed features may be implemented, in any combination and subcombination (including multiple dependent combinations and subcombinations), with one or more other features It will further be understood that any reference herein to subject matter known in the field does not, unless the contrary indication appears, constitute an admission that such subject matter is commonly known by those skilled in the art to which the present technology relates.

The invention claimed is:

1. An introducer sheath assembly for percutaneously delivering a medical device that maintains hemostasis in a patient, the introducer sheath assembly comprising:
   a sheath body; and
   a sheath hub assembly coupled to the sheath body, the sheath hub assembly comprising a hub, a hub cap, a hemostasis valve and, optionally, a foam,
   wherein the hemostasis valve comprises a single component comprising a valve portion and a frame portion, the frame portion defining a perimeter of the hemostasis valve and having a thickness that is greater than a thickness of the valve portion, the valve portion having a plurality of offset slits formed through the thickness of the valve portion,
   wherein the hub has a valve seating feature formed therein, the valve seating feature being a channel having an inner wall and an outer wall into which is received a portion of the hemostasis valve and a portion of the hub cap.

2. The introducer sheath assembly of claim 1, wherein the hemostasis valve is formed from an incompressible elastomer.

3. The introducer sheath assembly of claim 2, wherein the incompressible elastomer is selected from the group consisting of natural rubber, synthetic rubber, polyisoprene, polyurethane, silicone and a thermoplastic elastomer.

4. The introducer sheath assembly of claim 3, wherein the thermoplastic elastomer is one of a Styrenic block copolymer or a thermoplastic vulcanizate.

5. The introducer sheath assembly of claim 1, wherein the hub cap is sonically welded to the hub.

6. The introducer sheath assembly of claim 1, wherein the hub has a flush port formed therein.

7. The introducer sheath assembly of claim 1, wherein the valve seating feature is adapted to receive an extension of the frame portion of the hemostasis valve and a seating portion of the hub cap.

8. The introducer sheath assembly of claim 7, wherein the inner wall has a first height and the outer wall has a second height, wherein the second height is greater than the first height.

9. The introducer sheath assembly of claim 8, wherein the valve portion sits above the inner wall of the valve seating feature and the extension of the frame portion of the hemostasis valve extends into the valve seating feature.

10. The introducer sheath assembly of claim 7, wherein the seating portion of the hub cap is thicker at its proximal end than at its distal end.

11. The introducer sheath assembly of claim 7, wherein the extension of the frame portion comprises an O-ring.

12. The introducer sheath assembly of claim 7 wherein the extension of the frame portion has a uniform thickness.

13. The introducer sheath assembly of claim 12 wherein the extension of the frame portion extends from both sides of the valve portion.

14. The introducer sheath assembly of claim 7 wherein the extension of the frame portion is an undercut extension.

15. The introducer sheath assembly of claim 1, wherein the hub cap comprises a seating portion and the seating portion is either straight, stepped, or tapered.

16. The introducer sheath assembly of claim 15 wherein the seating portion is a stepped seating portion comprising a first, narrower step that seats between the hub and the frame portion and a second, wider step that seats against the valve portion.

17. The introducer sheath assembly of claim 15 wherein the seating portion is tapered and the taper is either parallel or non-parallel to a tapered portion of the valve portion in contact with the seating portion as the hub cap is assembled to the hemostasis valve and hub.

18. The introducer sheath assembly of claim 15, wherein the seating portion is straight and either parallel or non-parallel to the valve portion in contact with the seating portion as the hub cap is assembled to the hemostasis valve and hub.

\* \* \* \* \*